(12) United States Patent
Bonnyman et al.

(10) Patent No.: US 11,844,922 B2
(45) Date of Patent: Dec. 19, 2023

(54) ASEPTIC CONNECTOR FOR FLUID CONDUITS

(71) Applicant: Sunflower Therapeutics, PBC, Hingham, MA (US)

(72) Inventors: Alexandra Bonnyman, Weymouth, MA (US); Kerry R. Love, Somerville, MA (US); Larry Weiner, Newton, MA (US); John Christopher Love, Somerville, MA (US); Espir Kahatt, Carlsbad, CA (US); Ziad Al-Shamsie, San Diego, CA (US); Ben Reisman, Encinitas, CA (US); Alex Goldblatt, Winchester, MA (US)

(73) Assignee: SUNFLOWER THERAPEUTICS, PBC, Hingham, MA (US)

( * ) Notice: Subject to any disclaimer, the term of this patent is extended or adjusted under 35 U.S.C. 154(b) by 0 days.

(21) Appl. No.: 17/697,076

(22) Filed: Mar. 17, 2022

(65) Prior Publication Data
US 2022/0299144 A1 Sep. 22, 2022

Related U.S. Application Data

(60) Provisional application No. 63/163,167, filed on Mar. 19, 2021.

(51) Int. Cl.
*A61M 39/14* (2006.01)
*F16L 37/56* (2006.01)
(Continued)

(52) U.S. Cl.
CPC .......... *A61M 39/14* (2013.01); *A61M 39/105* (2013.01); *A61M 39/18* (2013.01);
(Continued)

(58) Field of Classification Search
CPC .... A61M 39/105; A61M 39/14; A61M 39/18; A61M 39/26; A61M 39/165; A61M 2039/1066; F16L 2201/44; F16L 2201/60
See application file for complete search history.

(56) References Cited

U.S. PATENT DOCUMENTS

| 4,917,668 | A | * | 4/1990 | Haindl | .................. A61M 39/26 |
| 5,423,761 | A | * | 6/1995 | Hein | ..................... A61M 39/26 |

(Continued)

FOREIGN PATENT DOCUMENTS

| CN | 109414577 A | 3/2019 |
| WO | WO 2014/160756 A1 | 10/2014 |
| WO | WO 2019/229202 A1 | 12/2019 |

OTHER PUBLICATIONS

International Search Report for related International Patent Application No. PCT/US22/20695 dated Jun. 9, 2022, 2 pages.
(Continued)

*Primary Examiner* — Zachary T Dragicevich
(74) *Attorney, Agent, or Firm* — Morgan, Lewis & Bockius LLP (57) ABSTRACT

An aseptic connector includes first and second matable housings each comprising a plurality of connectors for fluid conduits. The fluid conduits enter the housings and may be force-fitted onto barbs or flanges on one side of the connectors, or may instead be molded directly onto the connectors. When the housings are joined, the opposite sides of the connectors mate to form fluid seals, thereby establishing fluid pathways between now-connected sets of tubes.

17 Claims, 7 Drawing Sheets

(51) Int. Cl.
*A61M 39/10* (2006.01)
*A61M 39/08* (2006.01)
*A61M 39/18* (2006.01)

(52) U.S. Cl.
CPC .......... *F16L 37/56* (2013.01); *F16L 2201/44* (2013.01); *F16L 2201/60* (2013.01)

(56) References Cited

U.S. PATENT DOCUMENTS

| | | | |
|---|---|---|---|
| 5,533,996 | A | 9/1996 | Murphey et al. |
| 6,003,556 | A * | 12/1999 | Brugger ................ A61M 39/20 |
| 10,099,047 | B2 | 10/2018 | Gebauer |
| 10,946,183 | B2 | 3/2021 | Faldt et al. |
| 2010/0100056 | A1 * | 4/2010 | Cawthon ............ A61M 39/165 |
| 2014/0228809 | A1 * | 8/2014 | Wong ................ A61M 39/165 |
| 2015/0151102 | A1 | 6/2015 | Arduini et al. |
| 2018/0161568 | A1 * | 6/2018 | Banco ................. A61M 39/18 |
| 2019/0046783 | A1 * | 2/2019 | Raghavan ............ A61M 39/18 |
| 2019/0167971 | A1 | 6/2019 | Shevitz |

OTHER PUBLICATIONS

International Search Report and Written Opinion, PCT Application No. PCT/US22/20688, dated Aug. 23, 2022, 6 pages.

* cited by examiner

ASEPTIC CONNECTOR FOR FLUID CONDUITS

CROSS-REFERENCE TO RELATED APPLICATION

This application claims priority to and the benefit of, and incorporates herein by reference in its entirety, U.S. Ser. No. 63/163,167, filed on Mar. 19, 2021, the entire disclosure of which is hereby incorporated by reference.

FIELD OF THE INVENTION

The present invention relates, generally, to fluid transport and connections among fluid conduits in biological production processes.

BACKGROUND

Fluid systems may involve one or more networks of interconnected or parallel fluid paths. In full-scale (as opposed to microfluidic) systems, the fluid paths may be defined by tubing and various connections among tubing segments. Fluids may be moved through fluid systems using fluid pressure differentials produced by pumps, vacuum sources, or gravity. More generally, these systems commonly include components such as reservoirs, fittings, couplings, heat exchangers, sensors, filters, valves, seals, and the like. In the context of fluid systems involving, for example, bioprocessing, it may be desirable to have couplers that can aseptically connect a fluid flow path, e.g., from one piece of processing equipment to another along a sterile pathway or within parts of a piece of equipment or process.

Aseptic couplers must be able to make an aseptic connection outside a clean-room environment, enabling the created product-facing fluid paths to remain sterile before and during use (and particularly during the connection process). Any contact of the fluid path or a contact surface exposed to the environment or a user risks contamination, and the more prolonged the contact, the greater the risk will be. Merely packaging the connector in a sealed container or including removable seals does not eliminate the risk, since the connectors will be exposed at least to air for some period of time during the process of making a connection between fluid or product contact paths, allowing airborne contaminants to potentially enter the fluid path.

SUMMARY

Embodiments of the present invention facilitate selectable, bidirectional, aseptic connections among fluid conduits using a pair of matable housings each comprising a plurality of connectors for fluid conduits. The fluid conduits enter the housings and may be force-fitted onto barbs or flanges on one side of the connectors, or may instead be molded directly onto the connectors. When the housings are joined, the opposite sides of the connectors mate to form fluid seals, thereby establishing fluid pathways between now-connected sets of conduits. Importantly, the number of fluid-conduit connectors can be selected for a particular device configuration, and in a particular device, not all available connectors need be employed. This affords flexibility in terms of device configuration and actual use. Because a single housing set can afford a plurality of connections, the risks associated with independent connections are reduced.

In various embodiments, each of the housings includes a foil or other hermetic seal, and a first housing has a hinged door comprising a pair of serrated leaves. Mating of the first and second housings force the door leaves to swing open, breaking a seal between the two doors. The serrated leaves then pierce the seal of the second housings, enabling connection between the complementary fluid connectors within the housings.

Accordingly, in a first aspect, the invention relates to an aseptic connector for a plurality of fluid conduits. In various embodiments, the aseptic connector comprises first and second matable housings each comprising at least one connector for fluid conduits; and on the second housing, (i) at least one hinged door and (ii) a seal, wherein mating of the first and second housings causes the door to swing from a closed position into an open position to thereby pierce the seal and aseptically establish fluid communication between the connectors of the first housing and the connectors of the second housing.

In various embodiments, the hinged door(s) comprise a pair of serrated leaves. The seal may be disposed over the at least one hinged door.

In some embodiments, the first housing is sized to be received at least partially into the second housing. Each of the connectors may have a first end adapted to sealably receive a fluid conduit and a second end, opposite the first end, for mating with another connector.

In various embodiments, the leaves have complementary serrated edges in contact when the doors in the closed position. The aseptic connector may have a pierceable fluid seal over an interior of the first housing, and the fluid seal may be pierced upon mating of the first and second housings.

In some embodiments, the first housing includes a window therethrough and a first alignment mark on the window, and the second housing has second alignment mark thereon; registration of the first and second alignment marks indicates mating of the first-housing tubing connectors with the second-housing tubing connectors. Each of the first-housing tubing connectors may include a gasket surrounding a portion of the second end thereof, and the second ends of the first-housing tubing connectors may be receivable into the second ends of the second-housing tubing connectors; as a result, the gaskets provide fluidic seals.

In some embodiments, the first housing comprises a shroud and a frame bearing the first-housing connectors for fluid conduits, and may further include a pair of doors within the first housing for maintaining a sealed region between said doors and the pierceable fluid seal situated over the interior of the first housing. The doors may be openable upon introduction of the frame into the shroud.

In another aspect, the invention pertains to a method of fluid transfer. In various embodiments, the method comprises the steps of connecting a plurality of fluid conduits to first and second matable housings, where the second housing includes at least one hinged door and a seal; and mating the first and second housings, whereby the door is caused to swing from a closed position into an open position to pierce the seal and establish aseptic fluid connections between the connectors of the first housing and the connectors of the second housing.

The method may include one or more of the following features. The hinged door(s) may comprise a pair of serrated leaves. The fluid seal may be disposed over the at least one hinged door. The first housing may be sized to be received at least partially into the second housing. The door leaves have complementary serrated edges in contact with each other when the doors in the closed position, and a fluid seal over the interior of the second housing may be pierced upon mating of the first and second housings.

As used herein, the term "approximately" means±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

The foregoing and the following detailed description will be more readily understood when taken in conjunction with the drawings, in which.

DETAILED DESCRIPTION

In accordance with various embodiments of the invention, aseptic connection is conveniently achieved by joining complementary matable housings, each of which includes connectors for fluid conduits. When the housings are joined, the opposite sides of the connectors mate to form fluid seals, thereby establishing fluid pathways. The number of fluid-conduit connectors can be selected for a particular device configuration, and in a particular device, not all available connectors need be employed.

Figure 1A:
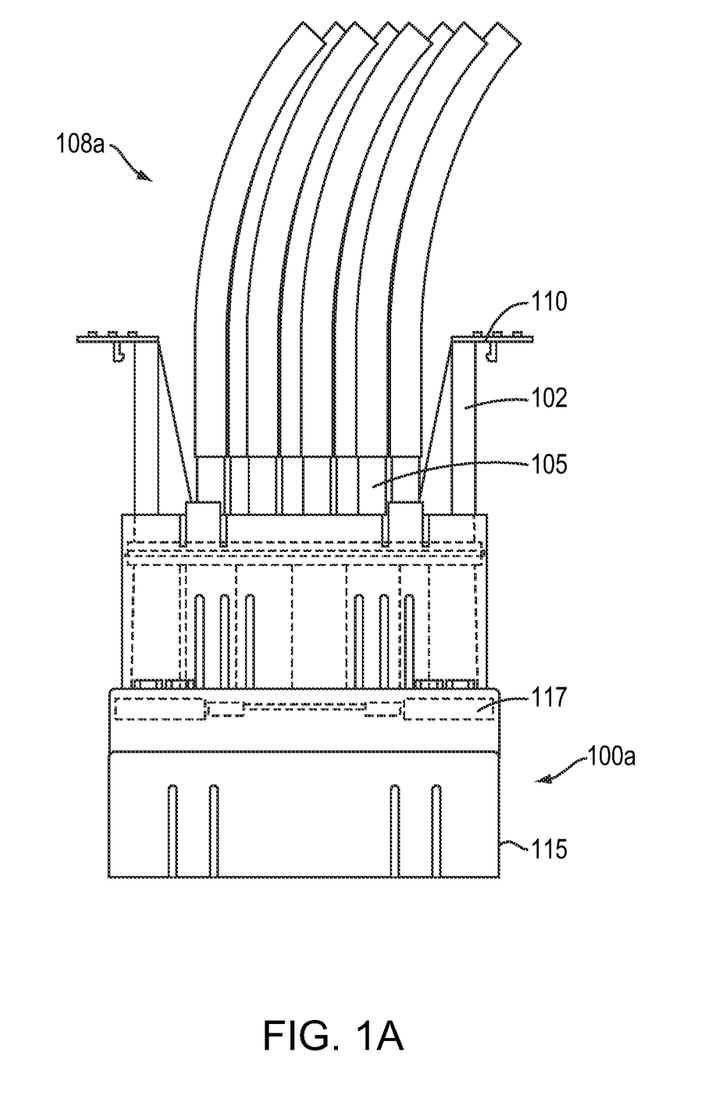
FIG. 1A is a partially transparent side elevation of the top housing member of an aseptic connector in accordance with embodiments of the invention.
Figure 1B:
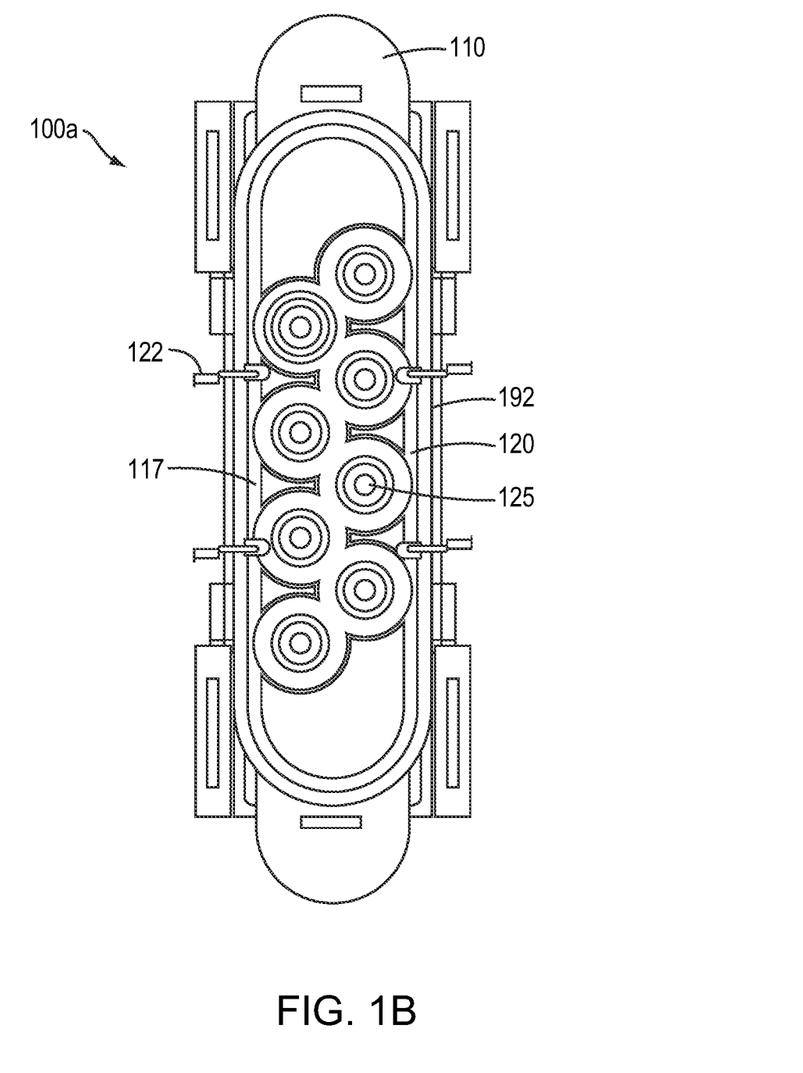
FIG. 1B is a partially transparent bottom plan view of the top housing member shown FIG. 1A.

Refer first to FIG. 1A, which shows an elevation of a first housing 100a in accordance with embodiments of the invention. The first housing 100a includes a frame 102 having mounted or molded thereon a series of fluid connectors 105. Each of the connectors 105 has a receiving end over which a flexible (e.g., silicone or rubber) tube conduit 108a may be force-fitted to form a fluid seal. As is conventional, this may be achieved by providing the outward-facing connector ends with one or more barbs, flanges, or other engagement members. In some embodiments, the frame 102 includes a pair of opposed handles 110 for guiding the connection between the frame 102 and a shroud 115. The shroud 115 includes a pair of hinged doors 117, 120, which are shown transparently in the bottom plan view of FIG. 1B. The doors 117, 120 are retained in the closed position by a series of torsion springs 122. As shown in FIG. 1B, the fluid connectors 105 terminate in engagement members 125 whose function is described below. FIGS. 1A and 1B illustrate the frame 102 and housing 115 prior to final assembly, which is described below.

Figure 1C:
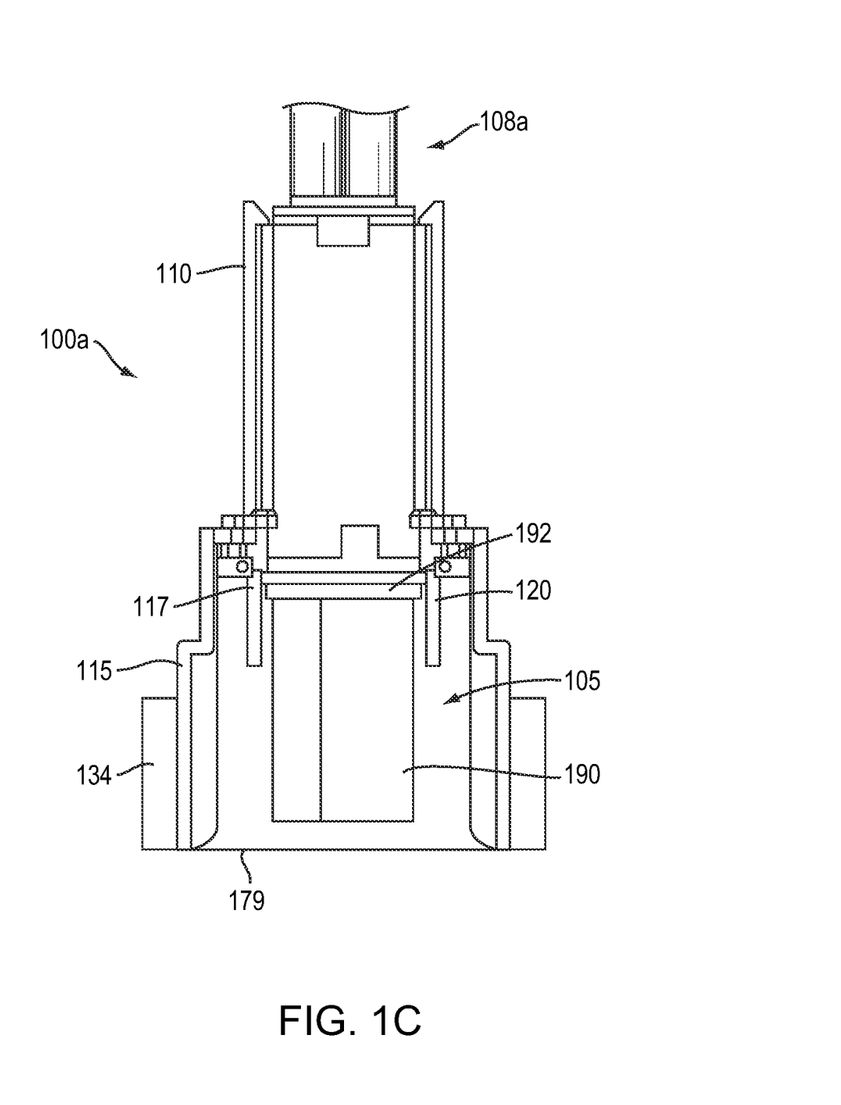
FIG. 1C is a partially transparent side elevation of the top housing member shown FIGS. 1A and 1B.
Figure 1D:
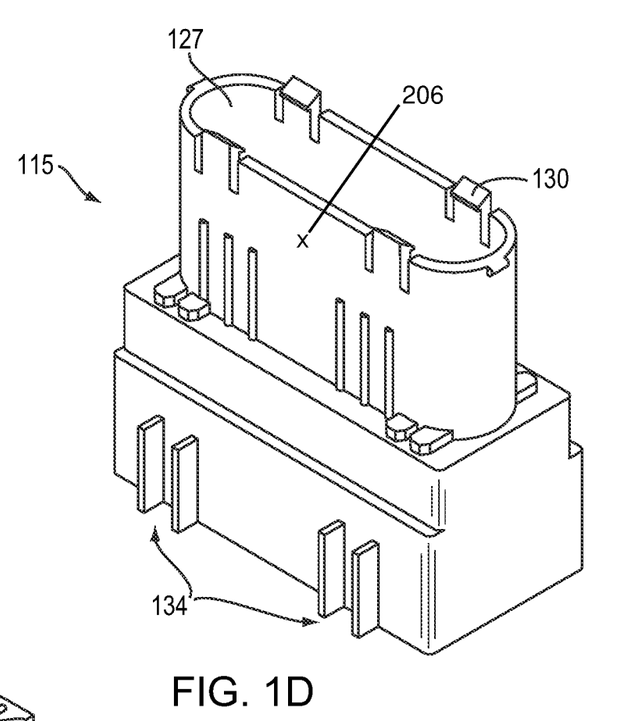
FIGS. 1D and 1E are isolated perspective views of the shroud and frame components, respectively, of the top housing member shown in FIGS. 1A-1C.
Figure 1E:
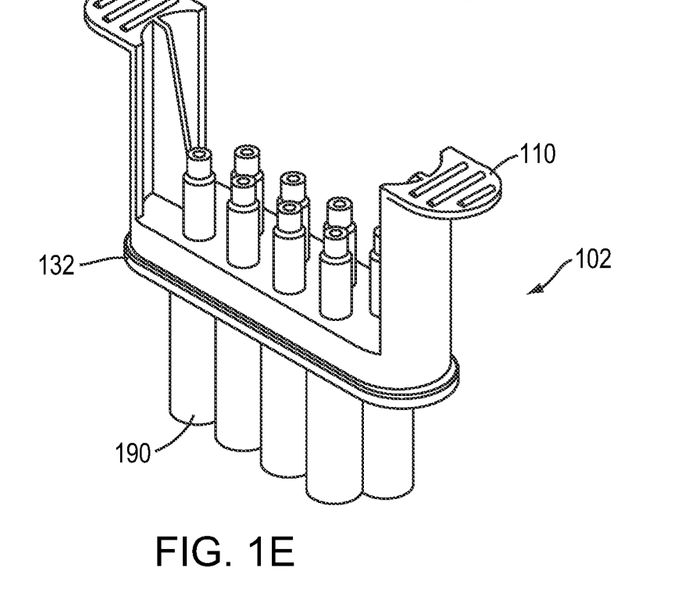

The housing 100a is assembled by driving the frame 102 into the housing 115 (e.g., using the handles 110) from the initial configuration shown in FIGS. 1A and 1B until the frame 102 locks into the final configuration shown in FIG. 1C. The lower ends 190 of the connectors 105 push through the doors 117, 120, which are retained in the open configuration by a peripheral rib 192. As illustrated in FIGS. 1D and 1E, the frame 102 is received within the well 127 of the shroud 115 until the locking tabs representatively indicated at 130 engage a peripheral tab 132 of the frame 102. The shroud 115 also includes five pairs alignment ribs 134. The asymmetric distribution of alignment ribs keys the frame 102 with the housing 115 so they can be connected in a single configuration.

Figure 2A:
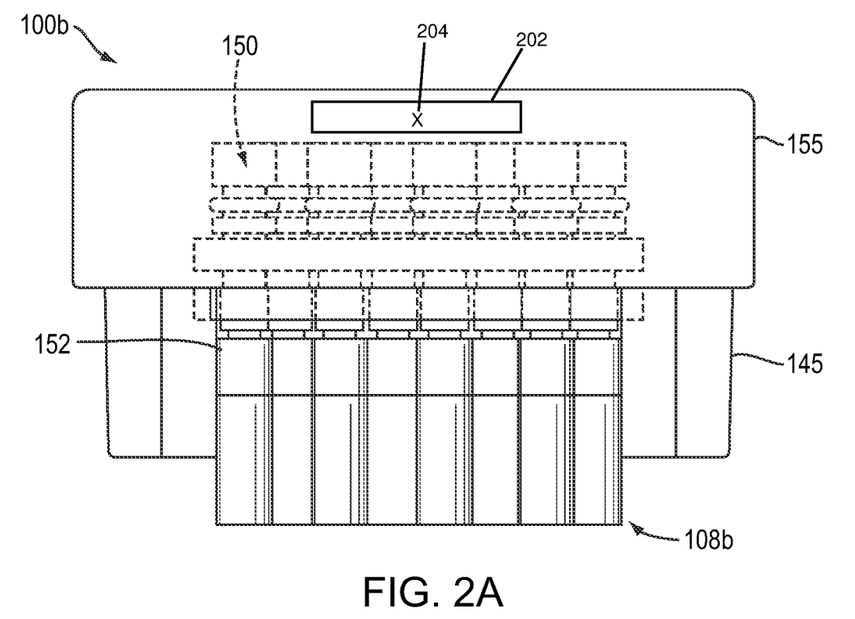
FIG. 2A is a partially transparent front elevation of a bottom housing member, matable with the top housing member shown in FIGS. 1A-1E, in accordance with embodiments of the invention.
Figure 2B:
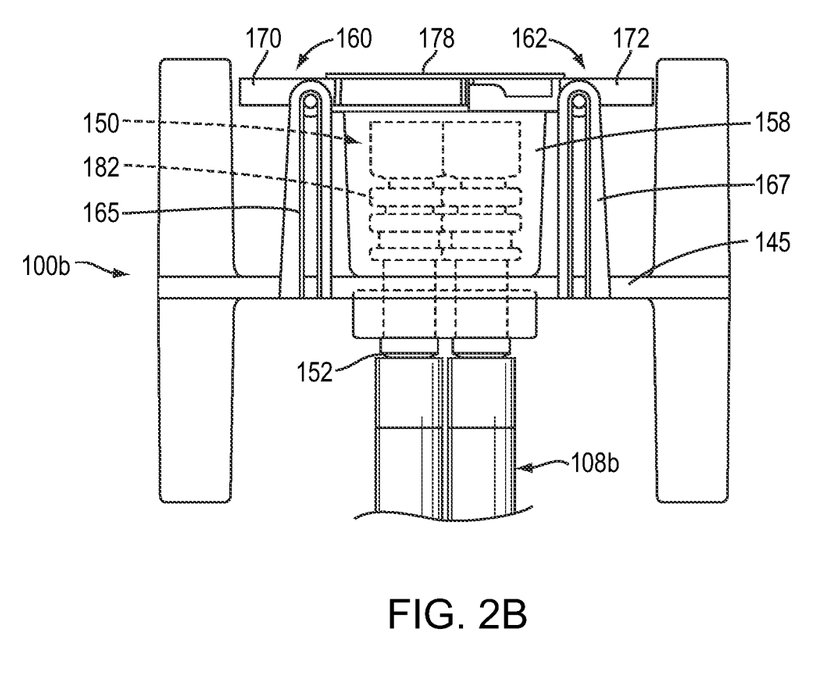
FIG. 2B is a partially transparent side view of the bottom housing member shown in FIG. 2A.
Figure 2C:
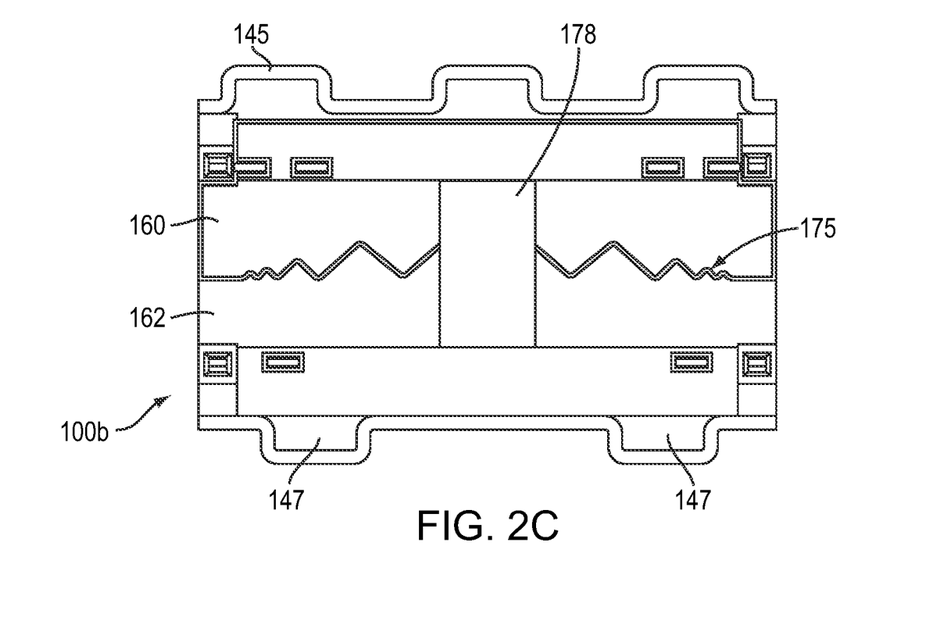
FIG. 2C is a plan view from the top of the bottom housing member shown in FIGS. 2A and 2B.

With reference to FIGS. 2A-2C, a second housing 100b is matable with the first housing 100a described above. The second housing 100b includes a frame 145 and a series of fluid connectors 150, described in greater detail below. Each of the connectors 150 has a receiving end 152 over which, once again, a flexible (e.g., silicone or rubber) tube conduit 108b may be force-fitted to form a fluid seal. A sidewall 155, shown fully in FIG. 2A and partially in FIG. 2B, surrounds the frame 145. The frame 145 is sized to receive the shroud 115 of the first housing 100a and includes a series of recesses 147 that each receive a pair of alignment ribs 134, keeping the housings aligned as the first housing 100a passes into the second housing 100b.

As best seen in FIG. 2C, at the top of the frame 145, and spanning the interior region 158 therewithin, are a pair of doors 160, 162. Each of the doors 160, 162 is hingedly mounted on a pair of end posts, one of which (for each door) is indicated at 165, 167. The posts are hinged to the doors 160, 162 at intermediate points so that force applied to outer segments 170, 172 of the doors causes them to swing upward into an open position. The seam 175 where the doors 160, 162 meet may be serrated or jagged. In the illustrated embodiment, a foil or other pierceable, substantially hermetic seal 178, only a portion of which is shown in FIG. 2C for clarity, overlies the entire top peripheral edge of the sidewall 155, forming a sealed interior region of the housing 100b containing the upper portions of the connectors 150. With the seal 178 overlying the doors 160, 162, the doors open upwardly by application of force to the outer segments 170, 172, and the serrated edges of the doors 160, 160 pierce and tear open the seal 178 to expose the connectors 150 in the interior housing region. A similar seal 179 (see FIG. 1C) may overlie the bottom peripheral edge of the shroud 115, forming a substantially hermetic interior region therein. The doors 117, 120 provide a second barrier against contamination.

Figure 3A:
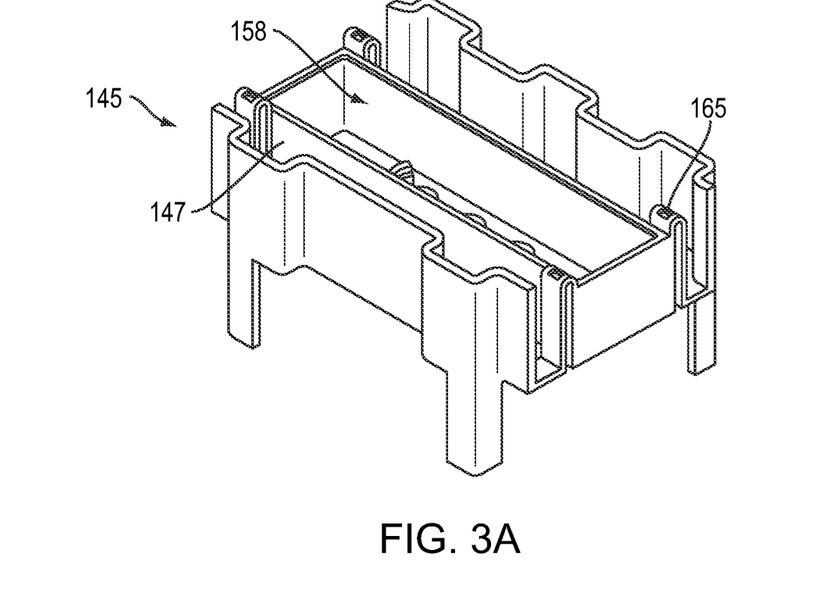
FIG. 3A is a perspective view of the frame component of the bottom housing member shown in FIGS. 2A-2C.
Figure 3B:
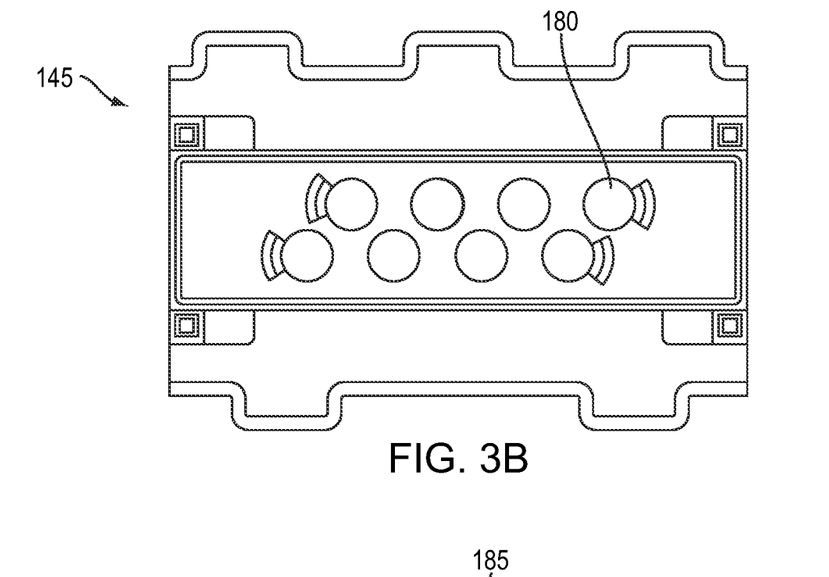
FIG. 3B is a plan view of the frame component shown in FIG. 3A.
Figures 4A, 4B:
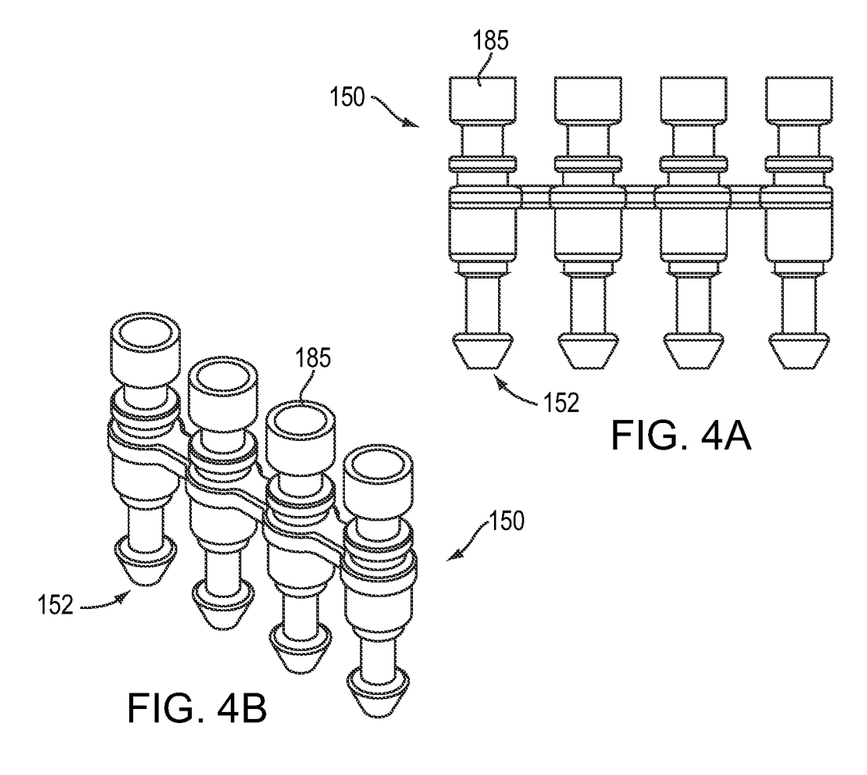
FIGS. 4A and 4B are elevation and perspective views, respectively, of four fluid connectors in accordance with embodiments of the invention.

FIGS. 3A and 3B show the frame 145 in isolation (without the surrounding sidewall 155) and the connectors 150. A series of connectors 150, four of which are representatively shown in FIGS. 4A and 4B, are installed and retained within the openings 180 of the frame 145. As illustrated, the receiving ends 152 are shaped to be received within a flexible tube but also to firmly retain the tube when it is forced thereover. As indicated in FIG. 2B, a sealing gasket 182 may be included along the neck region below a cup 185, which forms a shoulder over the neck region; the gasket 182, however, extends radially beyond the cup 185.

Prior to mating, the housings 100a, 100b remain sealed as described above by the seals 178, 179. As the housings 100a, 100b are brought together, the long bottom peripheral edges of the shroud 115 encounter the outer segments 170, 172 of the doors 160, 162 of the housing 100b. The elongated edges extend beyond the doors 160, 162 so that the bottom peripheral edge of the shroud 115 fully encloses, and receives, the posts 165 and the rectangular interior compartment 158 of the frame 145. As the shroud 115 travels into the housing 100b, its elongated bottom peripheral edges force the doors 160, 162 into the open configuration, piercing the seal 178 and admitting the lower ends 190 of the connectors 105 into the interior portion of the housing 100b to receive the cups 185 of the connectors 150—eventually fitting tightly over the gaskets 182. At this point the connection is complete: sealed fluid paths are established between the tubing conduits 108a, 108b. If desired, the housings 100a, 100b may include alignment marks. For example, the sidewall 155 may have a transparent window 202 with a first alignment mark 204 etched or printed thereon; a complementary alignment mark 206 may appear on the outer surface of the shroud 115, so that complete mating can be verified by visible alignment of the marks.

Numerous variations on the above-described configuration are possible. The seal 179 can be recessed to facilitate alignment between the housings 100a, 100b— i.e., to allow the alignment ribs 134 to enter the recesses 147 before force is applied to mate the housings 100a, 100b. The seal 178 can underlie the doors 160, 162, which may open inwardly instead of outwardly; that is, the doors 160, 162 can be opened downwardly by application of force (e.g., by the lower ends 190 of the connectors 105) to the seam between the doors. A puncturing device may drop from the shroud 115 to assist the doors 160, 162 in piercing the seal.

The various components described above may be fabricated from any suitable durable, solid, nonporous material such as stainless steel or other metal, or (more typically) a highly crosslinked polymer such as a polycarbonate, polypropylene or polysulfone. Disposable fluidic conduits often comprise or consist of biocompatible materials such as silicone tubing or other plastics.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. An aseptic connector for a plurality of fluid conduits, the aseptic connector comprising:
    first and second housings matable with one another and each comprising at least one connector for fluid conduits; and
    on the second housing, (i) at least one hinged door hingedly mounted on the second housing and (ii) a seal disposed at the second housing and configured for maintaining an interior region of the second housing sealed until mating of the first and second housings,
    wherein when mating of the first and second housings, the first housing causes the at least one hinged door to swing from a closed position into an open position to thereby pierce the seal and aseptically establish fluid communication between the at least one connector of the first housing and the at least one connector of the second housing.

2. The aseptic connector of claim 1, wherein the at least one hinged door on the second housing comprises a pair of serrated doors.

3. The aseptic connector of claim 1, wherein the seal is disposed over the at least one hinged door on the second housing.

4. The aseptic connector of claim 1, wherein the first housing is sized to be received at least partially into the second housing.

5. The aseptic connector of claim 1, wherein each of the at least one connector of the first housing and the at least one connector of the second housing has a first end adapted to sealably receive a fluid conduit and a second end, opposite the first end, for mating with another connector.

6. The aseptic connector of claim 2, wherein the serrated doors have serrated edges in contact when the serrated doors are in the closed position.

7. The aseptic connector of claim 1, further comprising a pierceable fluid seal over an interior of the first housing.

8. The aseptic connector of claim 7, wherein the pierceable fluid seal over the interior of the first housing is pierced upon mating of the first and second housings.

9. An aseptic connector for a plurality of fluid conduits, the aseptic connector comprising:
    first and second housings matable with one another and each comprising at least one connector for fluid conduits; and
    on the second housing, (i) at least one hinged door and (ii) a seal,
    wherein:
    mating of the first and second housings causes the at least one hinged door to swing from a closed position into an open position to thereby pierce the seal and aseptically establish fluid communication between the at least one connector of the first housing and the at least one connector of the second housing; and
    the first housing includes a window therethrough and a first alignment mark on the window and the second housing has second alignment mark thereon, registration of the first and second alignment marks indicating mating of the at least one connector of the first-housing with the at least one connector of the second-housing.

10. An aseptic connector for a plurality of fluid conduits, the aseptic connector comprising:
    first and second housings matable with one another and each comprising at least one connector for fluid conduits; and
    on the second housing, (i) at least one hinged door and (ii) a seal,
    wherein:
    mating of the first and second housings causes the at least one hinged door to swing from a closed position into an open position to thereby pierce the seal and aseptically establish fluid communication between the at least one connector of the first housing and the at least one connector of the second housing;

each of the at least one connector of the first housing and the at least one connector of the second housing has a first end adapted to sealably receive a fluid conduit and a second end, opposite the first end, for mating with another connector; and each of the at least one connector of the second housing includes a gasket surrounding a portion of the second end thereof, the second end of each of the at least one connector of the second housing being receivable into the second end of a corresponding connector in the at least one connector of the first housing whereby the gasket provides fluidic seals therebetween.

11. An aseptic connector for a plurality of fluid conduits, the aseptic connector comprising:

first and second housings matable with each other and each comprising at least one connector for fluid conduits;

a pierceable fluid seal over an interior of the first housing; and on the second housing, (i) at least one hinged door and (ii) a seal, wherein:

mating of the first and second housings causes the at least one hinged door to swing from a closed position into an open position to thereby pierce the pierceable fluid seal and aseptically establish fluid communication between the at least one connector of the first housing and the at least one connector of the second housing; and the first housing comprises a shroud and a frame bearing the at least one connector of the first housing for fluid conduits and further comprises a pair of doors within the first housing for maintaining a sealed region between said doors of the first housing and the pierceable fluid seal over the interior of the first housing, wherein said doors of the first housing are openable upon introduction of the frame into the shroud.

12. A method of fluid transfer comprising the steps of:

connecting a plurality of fluid conduits to first and second housings matable with one another, the second housing comprising at least one hinged door hingedly mounted on the second housing and a seal disposed at the second housing and configured for maintaining an interior region of the second housing sealed until mating of the first and second housings; and mating the first and second housings such that the first housing causes the at least one hinged door of the second housing to swing from a closed position into an open position to pierce the seal and establish aseptic fluid connections between at least one connector of the first housing and at least one connector of the second housing.

13. The method of claim 12, wherein the at least one hinged door of the second housing comprises a pair of serrated doors.

14. The method of claim 12, wherein the seal is disposed over the at least one hinged door of the second housing.

15. The method of claim 12, wherein the first housing is sized to be received at least partially into the second housing.

16. The method of claim 13, wherein the serrated doors have serrated edges in contact when the serrated doors are in the closed position.

17. The method of claim 12, wherein a fluid seal over an interior of the first housing is pierced upon mating of the first and second housings.

* * * * *